US009814518B2

(12) United States Patent
Couture et al.

(10) Patent No.: US 9,814,518 B2
(45) Date of Patent: *Nov. 14, 2017

(54) ASYMMETRICAL ELECTRODES FOR BIPOLAR VESSEL SEALING

(71) Applicant: COVIDIEN LP, Mansfield, MA (US)

(72) Inventors: Gary M. Couture, Ward, CO (US); Rebecca Coulson, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,900

(22) Filed: Nov. 21, 2016

(65) Prior Publication Data
US 2017/0065333 A1 Mar. 9, 2017

Related U.S. Application Data (63) Continuation of application No. 12/877,482, filed on Sep. 8, 2010, now Pat. No. 9,498,278.

(51) Int. Cl.
*A61B 18/14* (2006.01)
*A61B 17/00* (2006.01)
(Continued)

(52) U.S. Cl.
CPC ...... *A61B 18/1445* (2013.01); *A61B 18/1442* (2013.01); *A61B 2017/00526* (2013.01);
(Continued)

(58) Field of Classification Search
CPC ............ A61B 18/1442; A61B 18/1445; A61B 2018/1455; A61B 2018/1452; A61B 2018/00607; A61B 2018/00063
(Continued)

(56) References Cited

U.S. PATENT DOCUMENTS 3,987,795 A 10/1976 Morrison
4,043,342 A 8/1977 Morrison, Jr.
(Continued)

FOREIGN PATENT DOCUMENTS

DE 2415263 A1 10/1975
DE 02514501 A1 10/1976
(Continued)

OTHER PUBLICATIONS

Int'l Search Report EP 07 021646.0 dated Jul. 9, 2008.
(Continued)

*Primary Examiner* — Thomas Giuliani (57) ABSTRACT

Bipolar electrosurgical instrument having a first and a second opposing jaw member at a distal end thereof, wherein each jaw member includes an outer housing, and an inner tissue engaging surface corresponding to the inner tissue engaging surface of the opposing jaw. The instruments includes the ability to move the jaw members relative to one another from a first position wherein the jaw members are disposed in spaced relation relative to one another to a second position wherein the jaw members cooperate to grasp tissue. The jaws include asymmetrical electrodes disposed on the inner tissue engaging surfaces. A first contact region of the electrode has a greater surface area than that of the second contact region. During resection procedures wider electrodes impart improved sealing energy to the patient-side vessel while providing sufficient energy to resected tissue to effect hemostasis.

18 Claims, 7 Drawing Sheets

(51) Int. Cl.
  *A61B 18/00* (2006.01)
  *A61B 18/18* (2006.01)
  *A61B 90/00* (2016.01)
  *A61B 18/12* (2006.01)

(52) U.S. Cl.
  CPC ........... *A61B 2018/0063* (2013.01); *A61B 2018/00083* (2013.01); *A61B 2018/00178* (2013.01); *A61B 2018/00404* (2013.01); *A61B 2018/00428* (2013.01); *A61B 2018/00595* (2013.01); *A61B 2018/00607* (2013.01); *A61B 2018/00702* (2013.01); *A61B 2018/00732* (2013.01); *A61B 2018/00761* (2013.01); *A61B 2018/126* (2013.01); *A61B 2018/1412* (2013.01); *A61B 2018/1455* (2013.01); *A61B 2018/1861* (2013.01); *A61B 2090/3937* (2016.02)

(58) Field of Classification Search
  USPC ..................... 606/50–52, 205, 207
  See application file for complete search history.

(56) References Cited

U.S. PATENT DOCUMENTS

| | | |
|---|---|---|
| D249,549 S | 9/1978 | Pike |
| 4,202,337 A | 5/1980 | Hren et al. |
| 4,311,154 A | 1/1982 | Sterzer et al. |
| D263,020 S | 2/1982 | Rau, III |
| D295,893 S | 5/1988 | Sharkany et al. |
| D295,894 S | 5/1988 | Sharkany et al. |
| 4,754,757 A | 7/1988 | Feucht |
| D298,353 S | 11/1988 | Manno |
| D299,413 S | 1/1989 | DeCarolis |
| 4,802,476 A | 2/1989 | Noerenberg et al. |
| 4,807,621 A | 2/1989 | Hagen et al. |
| 4,873,973 A | 10/1989 | Hagen et al. |
| 4,878,906 A | 11/1989 | Lindemann et al. |
| 5,269,782 A | 12/1993 | Sutter |
| D343,453 S | 1/1994 | Noda |
| 5,324,289 A | 6/1994 | Eggers |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,454,809 A | 10/1995 | Janssen |
| 5,562,720 A | 10/1996 | Stern et al. |
| D384,413 S | 9/1997 | Zlock et al. |
| 5,766,166 A | 6/1998 | Hooven |
| 5,800,538 A | 9/1998 | Slepian et al. |
| 5,830,212 A | 11/1998 | Cartmell et al. |
| D402,028 S | 12/1998 | Grimm et al. |
| 5,947,977 A | 9/1999 | Slepian et al. |
| 5,951,549 A | 9/1999 | Richardson et al. |
| D416,089 S | 11/1999 | Barton et al. |
| 5,984,939 A | 11/1999 | Yoon |
| D424,694 S | 5/2000 | Tetzlaff et al. |
| D425,201 S | 5/2000 | Tetzlaff et al. |
| 6,071,283 A | 6/2000 | Nardella et al. |
| 6,086,586 A | 7/2000 | Hooven |
| 6,090,107 A | 7/2000 | Borgmeier et al. |
| 6,113,598 A | 9/2000 | Baker |
| 6,123,701 A | 9/2000 | Nezhat |
| 6,132,429 A | 10/2000 | Baker |
| 6,152,920 A | 11/2000 | Thompson et al. |
| 6,152,923 A | 11/2000 | Ryan |
| 6,176,857 B1 | 1/2001 | Ashley |
| 6,283,961 B1 | 9/2001 | Underwood et al. |
| D449,886 S | 10/2001 | Tetzlaff et al. |
| 6,296,640 B1 | 10/2001 | Wampler et al. |
| 6,350,262 B1 | 2/2002 | Ashley |
| D454,951 S | 3/2002 | Bon |
| 6,356,779 B1 | 3/2002 | Katzenmaier et al. |
| D457,958 S | 5/2002 | Dycus et al. |
| D457,959 S | 5/2002 | Tetzlaff et al. |
| 6,440,127 B2 | 8/2002 | McGovern et al. |
| 6,447,505 B2 | 9/2002 | McGovern et al. |
| 6,469,992 B1 | 10/2002 | Schieder |
| D465,281 S | 11/2002 | Lang |
| D466,209 S | 11/2002 | Bon |
| 6,514,252 B2 | 2/2003 | Nezhat et al. |
| 6,520,960 B2 | 2/2003 | Blocher et al. |
| 6,558,384 B2 | 5/2003 | Mayenberger |
| 6,558,385 B1 | 5/2003 | McClurken et al. |
| 6,562,048 B1 | 5/2003 | Fogarty et al. |
| 6,602,252 B2 | 8/2003 | Mollenauer |
| 6,623,482 B2 | 9/2003 | Pendekanti et al. |
| 6,656,177 B2 | 12/2003 | Truckai et al. |
| 6,692,493 B2 | 2/2004 | McGovern et al. |
| 6,701,172 B2 | 3/2004 | Katzenmaier et al. |
| 6,763,836 B2 | 7/2004 | Tasto et al. |
| D493,888 S | 8/2004 | Reschke |
| D496,997 S | 10/2004 | Dycus et al. |
| D499,181 S | 11/2004 | Dycus et al. |
| 6,821,273 B2 | 11/2004 | Mollenauer |
| 6,858,027 B2 | 2/2005 | Redtenbacher et al. |
| D502,994 S | 3/2005 | Blake, III |
| 6,887,240 B1 | 5/2005 | Lands et al. |
| 6,893,435 B2 | 5/2005 | Goble |
| 6,905,497 B2 | 6/2005 | Truckai et al. |
| D509,297 S | 9/2005 | Wells |
| 6,942,662 B2 | 9/2005 | Goble et al. |
| 7,011,657 B2 | 3/2006 | Truckai et al. |
| 7,033,354 B2 | 4/2006 | Keppel |
| 7,066,875 B2 | 6/2006 | Knighton et al. |
| 7,066,936 B2 | 6/2006 | Ryan |
| D525,361 S | 7/2006 | Hushka |
| D531,311 S | 10/2006 | Guerra et al. |
| 7,118,587 B2 | 10/2006 | Dycus et al. |
| D533,274 S | 12/2006 | Visconti et al. |
| D533,942 S | 12/2006 | Kerr et al. |
| 7,147,637 B2 | 12/2006 | Goble |
| 7,150,748 B2 | 12/2006 | Ebbutt et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| 7,211,084 B2 | 5/2007 | Goble et al. |
| D545,432 S | 6/2007 | Watanabe |
| D547,154 S | 7/2007 | Lee |
| 7,252,666 B2 | 8/2007 | Dycus |
| 7,270,664 B2 | 9/2007 | Johnson et al. |
| 7,276,068 B2 | 10/2007 | Johnson et al. |
| 7,311,560 B2 | 12/2007 | Ehr et al. |
| D564,662 S | 3/2008 | Moses et al. |
| 7,344,536 B1 | 3/2008 | Lunsford et al. |
| D567,943 S | 4/2008 | Moses et al. |
| 7,367,975 B2 | 5/2008 | Malecki et al. |
| 7,384,420 B2 | 6/2008 | Dycus et al. |
| D575,395 S | 8/2008 | Hushka |
| D575,401 S | 8/2008 | Hixson et al. |
| 7,442,194 B2 | 10/2008 | Dumbauld et al. |
| 7,449,021 B2 | 11/2008 | Underwood et al. |
| D582,038 S | 12/2008 | Swoyer et al. |
| 7,473,145 B2 | 1/2009 | Ehr et al. |
| 7,473,253 B2 | 1/2009 | Dycus et al. |
| 7,488,319 B2 | 2/2009 | Yates |
| 7,540,872 B2 | 6/2009 | Schechter et al. |
| 7,543,589 B2 | 6/2009 | Hooven |
| 7,591,794 B2 | 9/2009 | Lacoste et al. |
| 7,621,937 B2 | 11/2009 | Pipenhagen et al. |
| 7,641,651 B2 | 1/2010 | Nezhat et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,789,878 B2 * | 9/2010 | Dumbauld ......... A61B 18/1445 606/42 |
| 7,931,649 B2 | 4/2011 | Couture et al. |
| 8,070,748 B2 | 12/2011 | Hixson et al. |

(56) References Cited

U.S. PATENT DOCUMENTS

| | | | |
|---|---|---|---|
| 8,092,451 B2 | 1/2012 | Schechter et al. | |
| 8,187,273 B2 | 5/2012 | Kerr et al. | |
| 8,257,352 B2 | 9/2012 | Lawes et al. | |
| 8,277,446 B2 | 10/2012 | Heard | |
| 8,298,233 B2 | 10/2012 | Mueller | |
| 8,343,150 B2 | 1/2013 | Artale | |
| 8,348,948 B2 | 1/2013 | Bahney | |
| 8,409,247 B2 | 4/2013 | Garrison et al. | |
| 8,430,876 B2 * | 4/2013 | Kappus | A61B 18/1445 606/51 |
| 8,469,991 B2 | 6/2013 | Kerr | |
| 8,491,625 B2 | 7/2013 | Horner | |
| 8,491,626 B2 | 7/2013 | Roy et al. | |
| 8,512,336 B2 | 8/2013 | Couture | |
| 8,512,371 B2 * | 8/2013 | Kerr | A61B 17/295 606/171 |
| 8,540,749 B2 | 9/2013 | Garrison et al. | |
| 8,641,712 B2 | 2/2014 | Couture | |
| 8,641,713 B2 | 2/2014 | Johnson et al. | |
| 8,647,343 B2 | 2/2014 | Chojin et al. | |
| 8,652,135 B2 | 2/2014 | Nau, Jr. | |
| 8,663,222 B2 | 3/2014 | Anderson et al. | |
| 8,734,445 B2 | 5/2014 | Johnson et al. | |
| 8,814,864 B2 | 8/2014 | Gilbert | |
| 8,858,553 B2 * | 10/2014 | Chojin | A61B 17/285 606/51 |
| 8,888,775 B2 | 11/2014 | Nau, Jr. et al. | |
| 8,945,125 B2 | 2/2015 | Schechter et al. | |
| 8,968,357 B2 | 3/2015 | Mueller | |
| 9,005,200 B2 | 4/2015 | Roy et al. | |
| 9,017,372 B2 | 4/2015 | Artale et al. | |
| 9,028,495 B2 | 5/2015 | Mueller et al. | |
| 9,192,430 B2 | 11/2015 | Rachlin et al. | |
| 9,498,278 B2 * | 11/2016 | Couture | A61B 18/1442 |
| 2002/0072664 A1 | 6/2002 | Katzenmaier et al. | |
| 2002/0183734 A1 | 12/2002 | Bommannan et al. | |
| 2003/0018266 A1 | 1/2003 | Makin et al. | |
| 2003/0018270 A1 | 1/2003 | Makin et al. | |
| 2003/0018332 A1 | 1/2003 | Schmaltz et al. | |
| 2003/0032898 A1 | 2/2003 | Makin et al. | |
| 2003/0069502 A1 | 4/2003 | Makin et al. | |
| 2003/0092988 A1 | 5/2003 | Makin | |
| 2003/0109876 A1 | 6/2003 | Yamauchi | |
| 2003/0114851 A1 | 6/2003 | Truckai et al. | |
| 2004/0097919 A1 | 5/2004 | Wellman et al. | |
| 2004/0106918 A1 | 6/2004 | Cox et al. | |
| 2004/0167508 A1 | 8/2004 | Wham et al. | |
| 2004/0210282 A1 | 10/2004 | Flock et al. | |
| 2004/0249371 A1 | 12/2004 | Dycus et al. | |
| 2004/0260278 A1 | 12/2004 | Anderson et al. | |
| 2004/0260281 A1 | 12/2004 | Baxter et al. | |
| 2005/0004569 A1 | 1/2005 | Witt et al. | |
| 2005/0033277 A1 | 2/2005 | Clague et al. | |
| 2005/0043729 A1 | 2/2005 | Nahon et al. | |
| 2005/0113826 A1 | 5/2005 | Johnson et al. | |
| 2005/0113827 A1 * | 5/2005 | Dumbauld | A61B 18/1445 606/45 |
| 2005/0154387 A1 | 7/2005 | Moses et al. | |
| 2005/0203507 A1 | 9/2005 | Truckai et al. | |
| 2006/0004352 A1 | 1/2006 | Vaska et al. | |
| 2006/0052779 A1 | 3/2006 | Hammill | |
| 2006/0069386 A1 | 3/2006 | Dubnack et al. | |
| 2006/0069388 A1 | 3/2006 | Truckai et al. | |
| 2006/0200119 A1 | 9/2006 | Vaska et al. | |
| 2006/0212030 A1 | 9/2006 | McGaffigan | |
| 2006/0241580 A1 | 10/2006 | Mittelstein et al. | |
| 2006/0264922 A1 | 11/2006 | Sartor et al. | |
| 2006/0293656 A1 | 12/2006 | Shadduck et al. | |
| 2007/0060921 A1 | 3/2007 | Janssen et al. | |
| 2007/0078456 A1 | 4/2007 | Dumbauld et al. | |
| 2007/0106297 A1 | 5/2007 | Dumbauld et al. | |
| 2007/0118111 A1 | 5/2007 | Weinberg | |
| 2007/0156127 A1 | 7/2007 | Rioux et al. | |
| 2007/0167940 A1 | 7/2007 | Stevens-Wright | |
| 2007/0167943 A1 | 7/2007 | Janssen et al. | |
| 2007/0260235 A1 | 11/2007 | Podhajsky | |
| 2007/0260242 A1 | 11/2007 | Dycus et al. | |
| 2008/0004616 A1 | 1/2008 | Patrick | |
| 2008/0015575 A1 | 1/2008 | Odom et al. | |
| 2008/0021450 A1 | 1/2008 | Couture | |
| 2008/0039829 A1 | 2/2008 | Goldman et al. | |
| 2008/0039835 A1 | 2/2008 | Johnson et al. | |
| 2008/0045942 A1 | 2/2008 | Truckai et al. | |
| 2008/0058802 A1 | 3/2008 | Couture et al. | |
| 2008/0071261 A1 | 3/2008 | Orszulak | |
| 2008/0132890 A1 | 6/2008 | Woloszko et al. | |
| 2008/0140064 A1 | 6/2008 | Vegesna | |
| 2008/0140068 A1 | 6/2008 | Taimisto | |
| 2008/0140069 A1 | 6/2008 | Filloux et al. | |
| 2008/0140070 A1 | 6/2008 | Filloux et al. | |
| 2008/0140071 A1 | 6/2008 | Vegesna | |
| 2008/0140074 A1 | 6/2008 | Horne et al. | |
| 2008/0140112 A1 | 6/2008 | Horne | |
| 2008/0140113 A1 | 6/2008 | Taimisto et al. | |
| 2008/0147062 A1 | 6/2008 | Truckai et al. | |
| 2008/0172052 A1 | 7/2008 | Eder et al. | |
| 2008/0188844 A1 | 8/2008 | McGreevy et al. | |
| 2008/0188851 A1 | 8/2008 | Truckai et al. | |
| 2008/0200984 A1 | 8/2008 | Jodaitis et al. | |
| 2008/0243120 A1 | 10/2008 | Lawes et al. | |
| 2008/0281316 A1 | 11/2008 | Carlton et al. | |
| 2008/0312653 A1 | 12/2008 | Arts et al. | |
| 2009/0048596 A1 | 2/2009 | Shields et al. | |
| 2009/0088749 A1 | 4/2009 | Hushka et al. | |
| 2009/0105750 A1 | 4/2009 | Price et al. | |
| 2009/0112206 A1 | 4/2009 | Dumbauld et al. | |
| 2009/0171350 A1 * | 7/2009 | Dycus | A61B 18/1445 606/48 |
| 2009/0171353 A1 | 7/2009 | Johnson et al. | |
| 2009/0182328 A1 | 7/2009 | D'Amelio et al. | |
| 2009/0240250 A1 | 9/2009 | Hayashi et al. | |
| 2009/0248021 A1 | 10/2009 | McKenna | |
| 2009/0272784 A1 | 11/2009 | Farascioni | |
| 2009/0306660 A1 | 12/2009 | Johnson et al. | |
| 2009/0326530 A1 | 12/2009 | Orban, III et al. | |
| 2010/0030248 A1 | 2/2010 | Palmer et al. | |
| 2010/0036370 A1 | 2/2010 | Mirel et al. | |
| 2010/0036379 A1 | 2/2010 | Prakash et al. | |
| 2010/0042099 A1 | 2/2010 | Lunsford et al. | |
| 2010/0049194 A1 | 2/2010 | Hart et al. | |
| 2010/0057081 A1 | 3/2010 | Hanna | |
| 2010/0057082 A1 | 3/2010 | Hanna | |
| 2010/0057083 A1 | 3/2010 | Hanna | |
| 2010/0057084 A1 | 3/2010 | Hanna | |
| 2010/0179545 A1 | 7/2010 | Twomey et al. | |
| 2011/0009864 A1 * | 1/2011 | Bucciaglia | A61B 17/2909 606/52 |
| 2011/0054469 A1 * | 3/2011 | Kappus | A61B 18/1445 606/46 |
| 2011/0184405 A1 * | 7/2011 | Mueller | A61B 18/1445 606/41 |
| 2012/0283729 A1 * | 11/2012 | Kappus | A61B 18/1445 606/46 |
| 2012/0303023 A1 * | 11/2012 | Bucciaglia | A61B 17/2909 606/46 |
| 2013/0231662 A1 * | 9/2013 | Kappus | A61B 18/1445 606/46 |
| 2013/0296854 A1 * | 11/2013 | Mueller | A61B 18/1445 606/46 |
| 2013/0338666 A1 * | 12/2013 | Bucciaglia | A61B 17/2909 606/45 |

FOREIGN PATENT DOCUMENTS

| | | |
|---|---|---|
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |

(56) References Cited

FOREIGN PATENT DOCUMENTS

| | | |
|---|---|---|
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 102004026179 A1 | 12/2005 |
| DE | 202007009317 U1 | 8/2007 |
| EP | 0306123 B1 | 8/1993 |
| EP | 1159926 A3 | 3/2003 |
| EP | 1685806 A2 | 8/2006 |
| JP | 61501068 | 9/1984 |
| JP | 55106 | 1/1993 |
| JP | 540112 | 2/1993 |
| JP | 65502328 | 3/1994 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 1024051 | 1/1998 |
| JP | 11070124 | 3/1999 |
| JP | 11169381 | 6/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 2005110264 A3 | 4/2006 |

OTHER PUBLICATIONS

Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11180183.3 dated Nov. 21, 2011.
U.S. Appl. No. 12/876,731, filed Sep. 7, 2010.
U.S. Appl. No. 12/877,199, filed Sep. 8, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Intl Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Schmalt et al., US. Appl. No. 09/387,883, filed Sep. 1, 1999, abandoned.
Ryan, U.S. Appl. No. 09/591,328, filed Jun. 9, 2000, abandoned.
Sremcich et al., U.S. Appl. No. 12/336,970, filed Dec. 17, 2008, abandoned.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed Apr. 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun, 2, 2010.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.

(56) References Cited

OTHER PUBLICATIONS

Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.

* cited by examiner

ASYMMETRICAL ELECTRODES FOR BIPOLAR VESSEL SEALING

CROSS-REFERENCE TO RELATED APPLICATION

This application is a Continuation of U.S. patent application Ser. No. 12/877,482, filed on Sep. 8, 2010, now U.S. Pat. No. 9,498,278, the entire contents of which are hereby incorporated by reference.

BACKGROUND

1. Technical Field

The present disclosure relates to electrosurgical instruments and methods for performing surgical procedures and, more particularly, to a bipolar electrosurgical forceps having an asymmetrical electrode configuration.

2. Background of Related Art

A hemostat or forceps is a simple pliers-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue. Such electrosurgical forceps may be used during conventional (open) surgery and during minimally-invasive (e.g., endoscopic) surgery. During minimally-invasive surgery, endoscopic instruments are inserted into the patient through a cannula, or port, which has been made with a trocar. The benefits of minimally-invasive surgery are well known, and include decreased operative times, faster recovery, and improved outcomes.

Electrosurgical forceps commonly include an electrode on each opposing jaw surface. By controlling the intensity, frequency and duration of the electrosurgical energy applied through the jaw members, and by regulating the clamping force applied by the jaws to tissue, a surgeon can cauterize, coagulate, desiccate and/or simply reduce or slow bleeding of vessels and tissue. In particular, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal.

Many endoscopic surgical procedures require cutting blood vessels or vascular tissue. During certain endoscopic procedures, in particular, during resection procedures, vessels connecting the portion of the organ being resected must be cut to enable a surgeon to physically remove the organ from the patient's body. One portion of the severed vessel remains attached to the patient's vascular system, and the other portion of the severed vessel is removed with the resected organ.

Conventional vessel sealing instruments are often used during these types of resection procedures, and apply electrosurgical sealing energy equally to the patient side of the vessel and to the resected portion of the vessel. This approach may have drawbacks, because while the patient-side vessel seal must withstand in vivo fluid pressures, the resected-vessel seal need only prevent incidental leakage from the resected organ.

SUMMARY

The present disclosure relates to a bipolar forceps which includes a shaft having a first and second opposing jaw member at a distal end thereof and a drive assembly for moving the jaw members relative to one another from a first position, wherein the jaw members are disposed in spaced relation relative to one another, to a second position, wherein the jaw members cooperate to grasp tissue therebetween. The forceps are connected to a source of electrosurgical energy such that the jaw members are capable of conducting energy through tissue held therebetween to effect a tissue seal. A rotating assembly may also be included for rotating the jaw members about a longitudinal axis defined through the shaft. In embodiments, the forceps includes a selectively advanceable knife assembly for cutting tissue along the tissue seal.

The forceps include opposing electrodes disposed on inner facing surfaces of the jaw members. The first jaw member includes a first electrode and a second electrode. The first electrode has a surface area greater than that of the second electrode. The first and second electrodes may have any suitable shape, however, in an embodiment the first and second electrodes have an elongate shape, wherein the first and second electrodes have a similar length, and the first electrode has a width greater than that of the second electrode. The second jaw member includes counterpart (e.g., mirror-image) first and second electrodes such that the first, larger electrode of the first jaw member corresponds with the first, wider electrode of the second jaw member. Similarly, the second, narrower electrode of the first jaw member corresponds with the second, narrower electrode of the second jaw member. The first and second electrodes on each jaw may be electrically coupled or electrically independent.

The disclosed forceps may include an indicator to enable a surgeon to readily determine the position of the first and second electrodes. The indicator may be disposed on an outer surface of one or both jaws, on the shaft, and/or on the rotating assembly. The indicator may provide a visual indication (e.g., an icon, an arrow, a color, or other suitable visually-perceivable mark), a tactile indication (e.g., a raised area, a recessed area, a textured area, one or more "Braille-like" dimples, or other suitable feature perceivable by touch.)

During use, a surgeon may position the jaw assembly such that the side of the jaws corresponding to the wider electrode is positioned towards the patient-side vessel and the side of the jaws corresponding to the narrower electrode is positioned away from the patient-side vessel. In this manner, the wider electrodes may impart improved sealing energy to the patient-side vessel, and reduce the amount of wasted sealing energy to the portion of the vessel being resected.

The present disclosure describes an electrosurgical bipolar forceps having an electrode configuration for use in bipolar electrosurgical sealing and division, where the electrodes on one side of the jaws are larger than the electrodes on the opposite side of the jaws. The larger pair of electrodes are capable of effecting vessel sealing (e.g., capable of producing Ligasure™-quality tissue welds) while the smaller electrodes are well-adapted to effecting coagulation, e.g., to minimize blood in the surgical field. The disclosed instrument may include be equipped with an electrode and/or a blade capable of performing electrosurgical tissue division. The intended use of this device could be any surgical procedure where maintaining a quality seal is necessary on only one side of the device. An example of this is a polypectomy or lung wedge resection, where the excised portion of tissue would have minimal seal width and possibly reduced thermal spread for better assessment of disease states and margins. This may also allow the maximum seal width to be formed on the patient side of a resection while maintaining an overall smaller device footprint, a slimmer end effector and/or jaw assembly, and the like.

Desirably, at least one of the jaw members is made from a hard anodized aluminum having high dielectric properties. It is envisioned that the electrodes include a non-stick coating disposed thereon which is designed to reduce tissue adherence.

According to another aspect of the present disclosure, an electrosurgical forceps is disclosed. The disclosed forceps includes a shaft having a first and a second opposing jaw member at a distal end thereof. Each jaw member includes an outer housing, and an inner tissue engaging surface. Each jaw's inner tissue engaging surface corresponds to the inner tissue engaging surface of the opposite jaw. The forceps includes a drive assembly for moving the jaw members relative to one another from a first open position to a second closed position wherein the jaw members cooperate to grasp tissue therebetween. The jaws include an electrode disposed on the inner tissue engaging surface having a first contact region disposed adjacent to a first edge of the inner tissue engaging surface, and a second contact region disposed adjacent to a second edge of the inner tissue engaging surface. The surface area of the first contact region is greater than the surface area of the second contact region.

According to another embodiment, disclosed is an electrosurgical forceps having a shaft and a pair of opposing jaw members at a distal end thereof. Each jaw member includes an outer housing, and an inner tissue engaging surface corresponding to the inner tissue engaging surface of the opposing jaw. The forceps includes a drive assembly for moving the jaw members relative to one another from a first, open position to a second, closed position wherein the jaw members cooperate to grasp tissue therebetween. Each jaw includes a first electrode disposed on an inner tissue engaging surface and disposed adjacent to a first edge of the inner tissue engaging surface, and a second electrode disposed on an inner tissue engaging surface and disposed adjacent to a second edge of the inner tissue engaging surface. The surface area of the first electrode is greater than the surface area of the second electrode.

Also disclosed is a method of operating an electrosurgical forceps, comprising the steps of providing an electrosurgical forceps having a shaft having a first and a second opposing jaw member at a distal end thereof. Each jaw member of the provided forceps includes an outer housing, and an inner tissue engaging surface corresponding to the inner tissue engaging surface of the opposing jaw. The provided forceps includes a drive assembly for moving the jaw members relative to one another from a first, open position to a second, closed position wherein the jaw members cooperate to grasp tissue therebetween. A first electrode is operably coupled to a source of electrosurgical energy and disposed on the inner tissue engaging surface of the first jaw. The first electrode has a first contact region disposed adjacent to a first edge of the inner tissue engaging surface of the first jaw, and a second contact region disposed adjacent to a second edge of the inner tissue engaging surface of the first jaw. The surface area of the first contact region of the first electrode is greater than the surface area of the second contact region thereof. A second electrode is operably coupled to a source of electrosurgical energy and disposed on the inner tissue engaging surface of the second jaw. The second electrode has a first contact region disposed adjacent to a first edge of the inner tissue engaging surface of the second jaw, and a second contact region disposed adjacent to a second edge of the inner tissue engaging surface of the second jaw. The surface area of the first contact region of the second electrode is greater than the surface area of the second contact region thereof.

The method includes the steps of closing the jaws to grasp tissue therebetween, and applying electrosurgical energy to tissue via the first electrode and the second electrode to cause a change to the tissue.

BRIEF DESCRIPTION OF THE DRAWINGS

Various embodiments of the subject instrument are described herein with reference to the drawings wherein.

DETAILED DESCRIPTION

Particular embodiments of the present disclosure are described hereinbelow with reference to the accompanying drawings, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user. Similar reference numbers are used for elements that are the same or similar to elements illustrated or described herein. In addition, as used herein, terms referencing orientation, e.g., "top", "bottom", "up", "down", "left", "right", "clockwise", "counterclockwise", "upper", "lower", and the like, are used for illustrative purposes with reference to the figures and features shown therein. It is to be understood that embodiments in accordance with the present disclosure may be practiced in any orientation without limitation.

Figure 1:
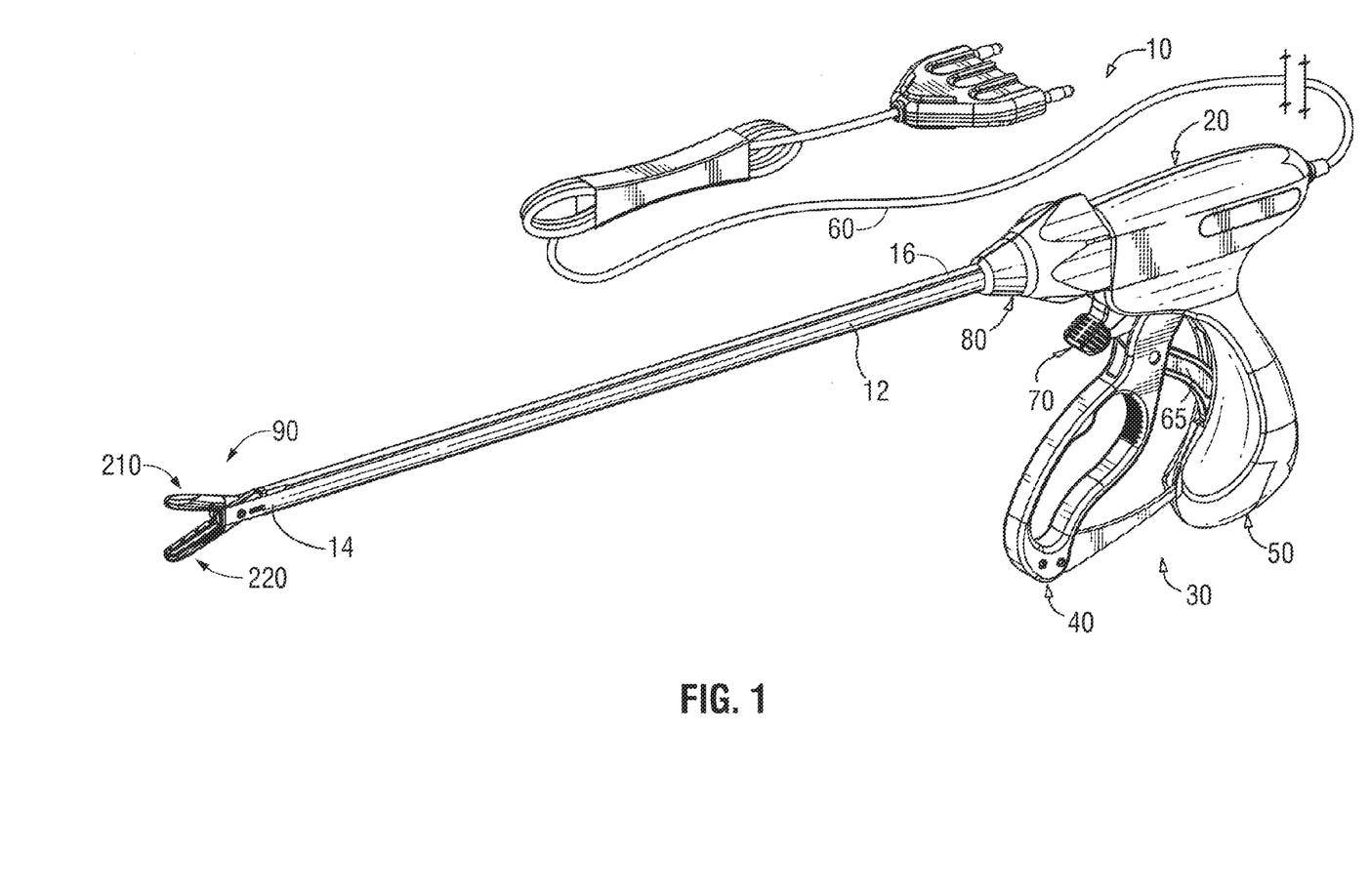
FIG. 1 is a left, perspective view of an embodiment of a bipolar electrosurgical instrument in accordance with the present disclosure showing a housing, a shaft and a jaw assembly having an asymmetrical electrode.

Referring to FIG. 1, a bipolar surgical instrument 10 is shown generally and includes a housing 20, a handle assembly 30, a trigger assembly 70, a rotating assembly 80, and an end effector assembly 90, such as, without limitation, a forceps or hemostat, which mutually cooperate to grasp, seal, and/or divide tubular vessels and vascular tissue. As shown, handle assemblies 30 of instrument 10 are of the pistol grip-type, however, any suitable type of handle is envisioned within the scope of the present disclosure. The handle assembly 30 offers a surgeon a gripping position from which to grasp instrument 10 and to transmit a clamping pressure to end effector assembly 90. Instrument 10 includes a shaft 12, which has a distal end 14 configured to mechanically engage end effector assembly 90, and a proximal end 16 configured to mechanically engage housing 20.

Figure 2:
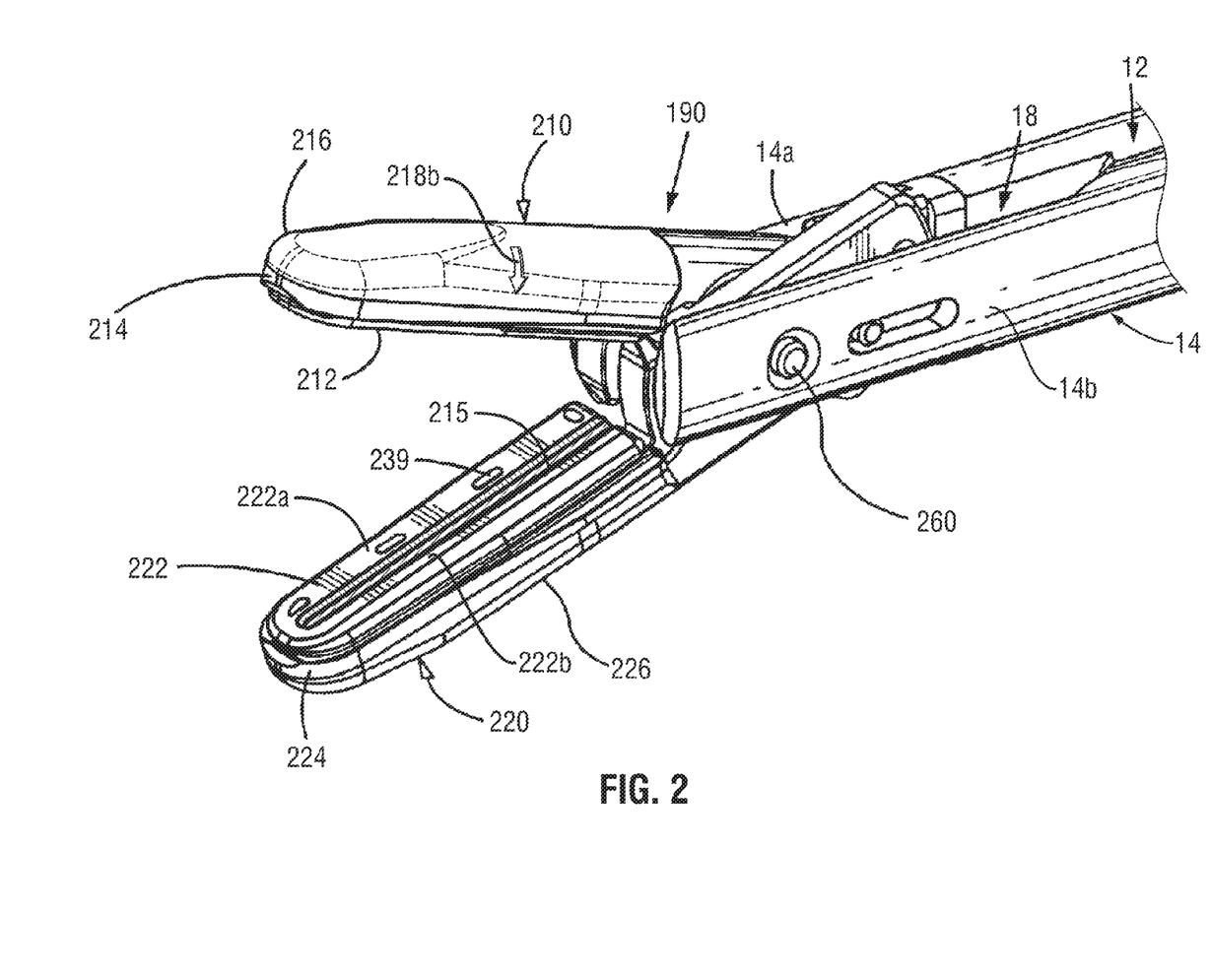
FIG. 2 is an enlarged, left perspective view of an embodiment of a jaw assembly having an asymmetrical electrode in accordance with the present disclosure.
Figure 3:
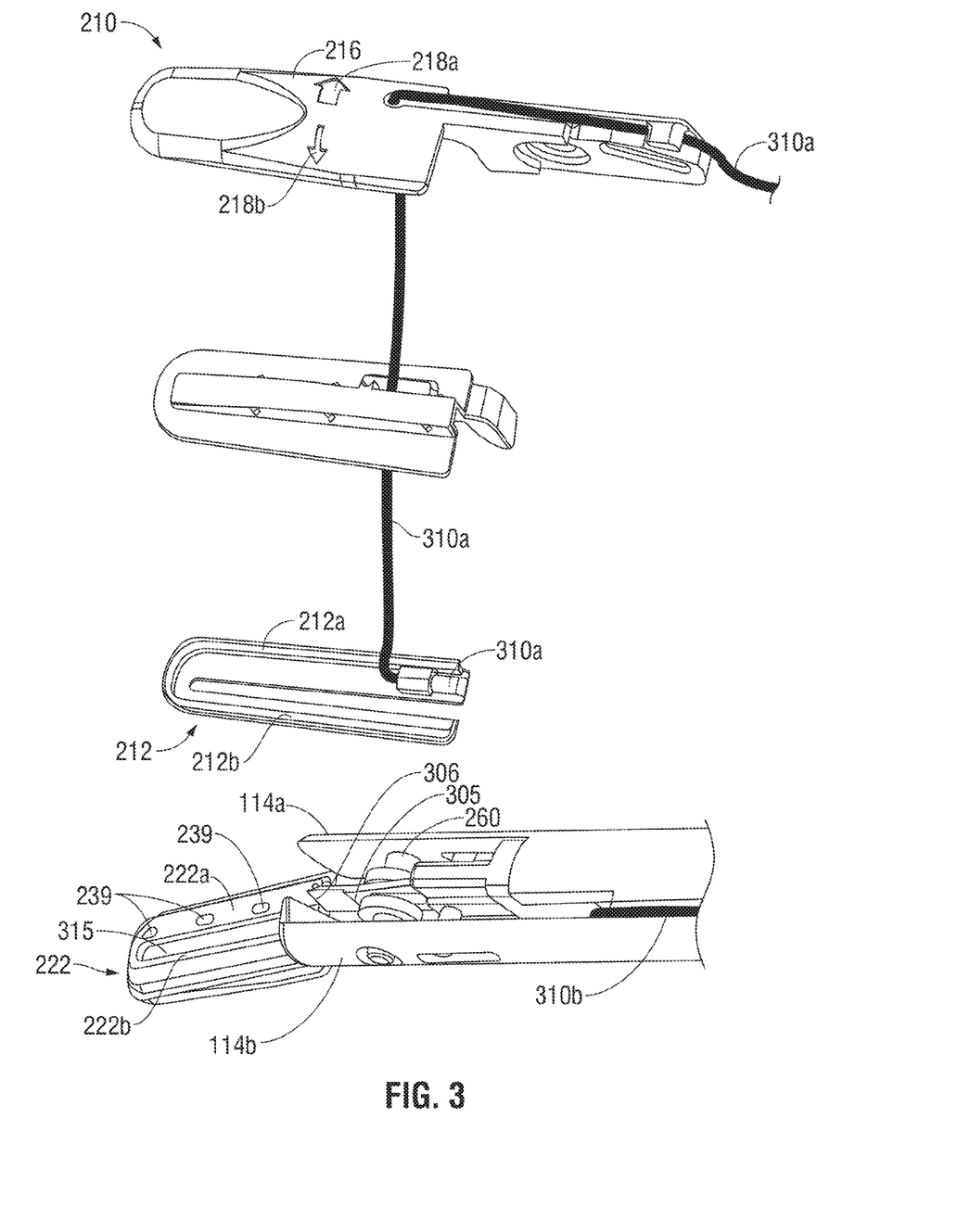
FIG. 3 is an enlarged, partially-exploded view of the FIG. 2 embodiment of a jaw assembly having an asymmetrical electrode in accordance with the present disclosure.

As depicted in FIG. 1, shaft 12 of instrument 10 is relatively elongated. The relatively elongated shaft 12 of instrument 10 enables instrument 10 to be used in performing endoscopic surgical procedures. Shaft 12 may alternatively have a shorter, or longer, shaft than that shown in FIG. 1, which may be desirably utilized in various endoscopic and/or open surgical procedures. Rotating assembly 80 is attached to a distal end of housing 20 and is rotatable in either direction about a longitudinal axis of the shaft 12. In some embodiments, rotating assembly 80 is rotatable approximately 180 degrees in either direction about a longitudinal axis of the shaft 12. Rotation of rotating assembly 80 correspondingly rotates jaw assembly 90 about the longitudinal axis of shaft 12. In some embodiments, as seen in FIGS. 2 and 3, shaft 12 is bifurcated at distal end 14 thereof to form ends 14a and 14b, which are configured to receive jaw assembly 90.

Instrument 10 further may include an electrical cable 60 extending from housing 20 which couples instrument 10 to a source of electrosurgical energy, e.g., a generator (not explicitly shown). In some embodiments, a source of electrosurgical energy (not explicitly shown), and/or a power source, such as without limitation, a rechargeable battery (not shown), may be included within instrument 10, e.g., within the housing 20 thereof.

Handle assembly 30 includes a first handle 50 and a second handle 40. Second handle 40 is selectively movable about a pivot (not shown) from a first position in spaced relation relative to first handle 50 to a second position in closer proximity relative to first handle 50 which imparts movement of jaw members 210 and 220 relative to one another, e.g., from an open to closed position about tissue. As shown in greater detail in FIG. 2, jaw assembly 90 is attached to distal end 14 of shaft 12 and includes a pair of opposing jaw members 210 and 220. For illustrative purposes, jaw member 210 may be referred to as an upper jaw member 210 and jaw member 220 may be referred to as a lower jaw member 220. First and second handles 40, 50 are ultimately connected to a drive rod (not explicitly shown) which, together, mechanically cooperate to impart movement of jaw members 210, 220 from an open position wherein the jaw members 210, 220 are disposed in spaced relation relative to one another, to a clamping or closed position wherein, e.g., jaw members 210, 220 cooperate to grasp tissue therebetween.

Jaw members 210 and 220 are seated within a cavity 18 defined between bifurcated ends 14a and 14b of shaft 12. Jaw members 210 and 220 include mutually corresponding component features which cooperate to permit rotation about a pivot pin 260 to effectively grasp, seal, and/or divide tissue. Jaw members 210, 220 each include a jaw housing 216, 226, an insulative substrate or insulator 214, 224 and an electrically conductive surface or electrode 212, 222. Insulators 214, 224 are configured to securely engage the electrodes 212, 224. This may be accomplished by, e.g., stamping, by overmolding, by overmolding a stamped electrically conductive sealing plate and/or by overmolding a metal injection molded seal plate. Such manufacturing techniques produce a jaw assembly having an electrode 212, 222 which is substantially surrounded by an insulating substrate 214, 224. Insulating substrate 214, 224, electrode 212, 222, and the outer, non-conductive jaw housings 216, 226 are preferably configured to limit and/or reduce many of the known undesirable effects related to tissue sealing, e.g., flashover, thermal spread and stray current dissipation. Alternatively, jaw members 210 and 220 may be manufactured from a ceramic-like material and electrically conductive surfaces 212, 222 coated onto the ceramic-like jaw members 210, 220.

Electrodes 212, 222 may also include an outer peripheral edge which has a radius and insulators 214, 224 that meet electrodes 212, 222 along an adjoining edge which is generally tangential to the radius and/or meets along the radius. At the interface, electrodes 212, 222 are raised relative to insulator 214, 224.

Jaw members 210, 220 may be electrically isolated from one another such that electrosurgical energy can be effectively transferred through the tissue to form the seal. Electrodes 212, 222 of jaw members 210, 220, respectively, may be relatively flat to avoid current concentrations at sharp edges and to avoid arcing between high points. In addition, and due to the reaction force of the tissue when engaged, jaw members 210, 220 may be manufactured to resist bending. For example, jaw members 210, 220 may be tapered along the width thereof which is advantageous for two reasons: 1) the taper will apply constant pressure for a constant tissue thickness at parallel, and 2) the thicker proximal portion of jaw members 210, 220 will resist bending due to the reaction of the tissue.

Jaw members 210, 220 may be curved in order to reach specific anatomical structures. For example, dimensioning jaws 210, 220 at an angle of about 50 degrees to about 70 degrees is preferred for accessing and sealing specific anatomical structures relevant to prostatectomies and cystectomies, e.g., the dorsal vein complex and the lateral pedicles.

As best seen in example embodiments shown in FIGS. 2 and 3, electrodes 212, 222 include a first, larger contact area 212a, 222a and a second smaller contact area 212b, 222b. Larger contact areas 212a, 222a are arranged in a mutually corresponding configuration with respect to jaw members 210, 220 such that contact area 212a mates with contact area 222a when jaw members 210, 220 are in a closed position, e.g., when grasping tissue therebetween. Similarly, smaller contact areas 212b and 222b are arranged in a mutually corresponding configuration such that contact area 212b mates with contact area 222b when jaw members 210, 220 are in a closed position. During use, the larger contact areas of electrodes 212a, 222a may be used to grasp the patient-side of a vessel and/or the smaller contact areas of electrodes 212b, 222b may be used to grasp tissue, vessels, etc. slated for resection. During a vessel sealing procedure, the larger contact areas of electrodes 212a, 222a enable the delivery of electrosurgical energy at a density sufficient to form a burst-resistant vessel seal on the patient side of the jaws. Conversely, the narrower electrodes 212b, 222b enable the delivery of electrosurgical energy to the resection side of the jaw members 210, 200 to produce a smaller seal.

In one envisioned embodiment, the size ratio of the larger contact area 212a, 222a to the second smaller contact area 212b, 222b is about 3:1, however, the size ratio may be in a range of about 1.2:1 to about 10:1 and in some embodiments may range up to 100:1 or greater. In some embodiments, the width ratio of the width of the larger contact area 212a, 222a to the second smaller contact area 212b, 222b is about 3:1, however, the width ratio may be in a range of about 1.2:1 to about 10:1 and in some embodiments may range up to 100:1 or greater.

A conductor 310a electrically couples electrode 212 (which includes wide electrode 212a and narrow electrode 212b) to a source of electrosurgical energy as described hereinabove. Similarly, conductor 310b electrically couples electrode 222 (e.g., wide electrode 222a and narrow electrode 222b) to a source of electrosurgical energy.

In another aspect, jaw housings 216, 226 include a visual indicator 218a and 218b that is configured to enable a surgeon to readily ascertain jaw member orientation. In the example embodiment depicted in FIGS. 2 and 3, visual indicator 218a includes an intaglio arrowhead icon formed in an outer surface of jaw housing 216 that indicates the position of the wide electrode 212a. Similarly, visual indicator 212b includes an intaglio arrowhead icon formed in an outer surface of jaw housing 216 that indicates the position of narrow electrode 212b. As shown in the drawings, indicators 218a and 218b indicate the wide and narrow electrodes 212a, 212b by using corresponding wide and narrow arrows 218a, 218b. The visual indicators 218a, 218b may include arrows, or may include any other icon to represent the wide and narrow electrodes 212a, 212b, respectively. The design of visual indicators 218a, 218b may include a mnemonic element that enables "at a glance" intuitive interpretation by the surgeon. Other envisioned indicators include a large circle/small circle, single bar/double bar, pictograph, different colors, and so forth. While not explicitly shown in the figures, visual indicators may be included in lower jaw member 226 to enable a surgeon to identify electrode orientation regardless of the rotated position of the jaw member 216, 226. Additionally or alternatively, visual indicators 218a, 218b may be formed by any suitable marking technique, e.g., in raised relief, laser etching, stamping, molding, machining, pigment, ink, dye, overmolding, and the like. Additionally or alternatively, visual indicators 218a, 218b may be positioned on shaft 12 and/or rotating assembly 80 as long as they correspond to jaw member orientation.

As seen in FIGS. 2 and 3, in order to achieve a desired gap range (e.g., about 0.001 to about 0.006 inches) and apply a desired force to seal the tissue, at least one jaw member 210 and/or 220 includes one or more stop members 239 that limit the movement of the two opposing jaws 210, 220 relative to one another. Each stop member 239 is made from an insulative material and is dimensioned to limit opposing movement of jaw members 210, 220 to within the above gap range.

A knife channel 215 may be defined through the center of jaw member 220 such that a knife 305 having a distal cutting edge 306 may cut through the tissue grasped between jaw members 210 and 220 when jaw members 210 and 220 are in a closed position, as illustrated with reference to FIGS. 6A and 6B. Details relating to the knife channel 215, knife 305, trigger assembly 70, and a knife actuation assembly associated therewith (not explicitly shown) are explained in limited detail herein and explained in more detail with respect to commonly-owned U.S. Pat. Nos. 7,156,846 and 7,150,749 to Dycus et al.

Housing 20 is formed from two housing halves that engage one another via a series of mechanical interfaces to form an internal cavity for housing the internal working components of instrument 10. For the purposes herein, the housing halves are generally symmetrical and, unless otherwise noted, a component described with respect to a first of the housing halves will have a similar component which forms a part of a second of the housing halves.

As mentioned above, first handle 50 and second handle 40 of handle assembly 30 cooperate with one another and with housing 20 to activate a first mechanical linkage (not shown) which, in turn, actuates a drive assembly (not shown) for imparting movement of opposing jaw members 210, 220 relative to one another to grasp tissue therebetween.

Figure 6A:
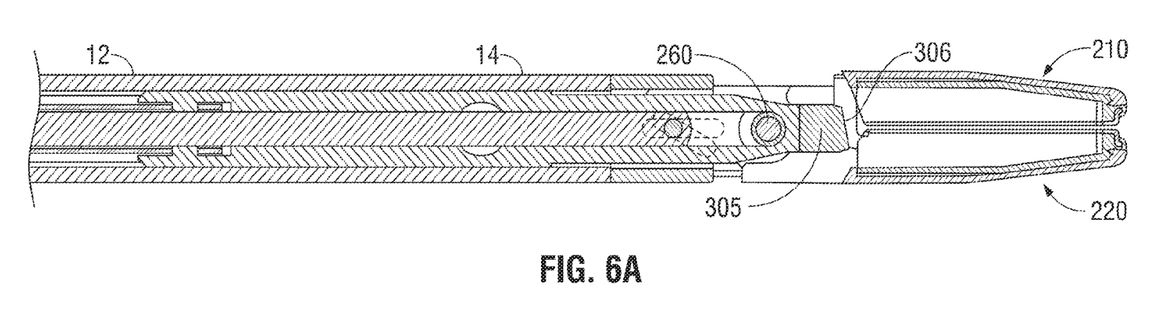
FIG. 6A is an enlarged, cross-sectional view of the distal end of a jaw assembly in accordance with the present disclosure showing a knife assembly in a proximal position prior to the actuation thereof.
Figure 6B:
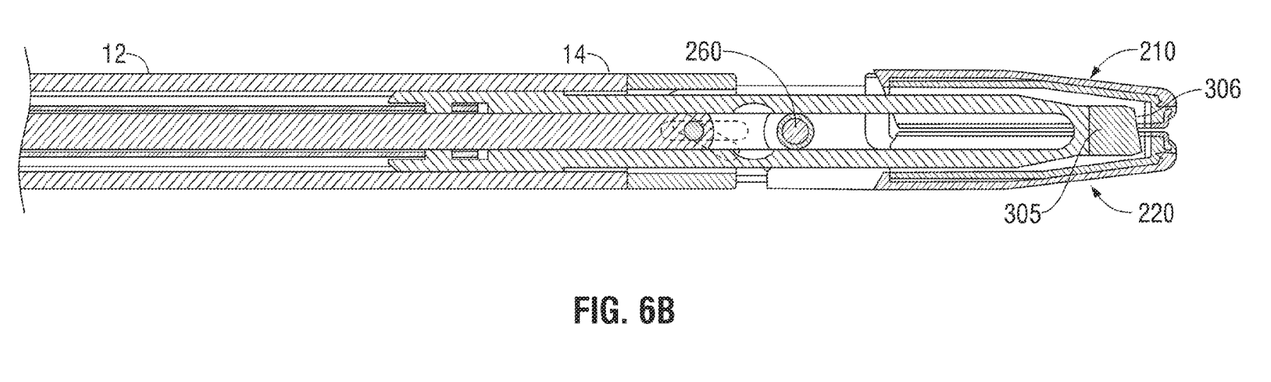
FIG. 6B is an enlarged, cross-sectional view of the distal end of a jaw assembly in accordance with the present disclosure showing a knife assembly in a distal position subsequent to the actuation thereof.

Handle assembly 130 further includes a trigger assembly 70 that cooperates with a knife actuation assembly (not explicitly shown) which enables the extension of knife 305 from a first, proximal, position as depicted in FIG. 6A, to a second, distal position as depicted in FIG. 6B to sever tissue grasped between jaw members 210, 220. Knife 305 travels within knife channel 215 formed within jaws 210, 220. In an embodiment, trigger assembly 70 may include a lockout (not explicitly shown) that inhibits actuation of knife 305 while jaws 210, 220 are in an open position.

As discussed above, by controlling the intensity, frequency and duration of the electrosurgical energy applied to the tissue, the surgeon can cauterize, coagulate, desiccate, seal and/or simply reduce or slow bleeding. In addition, the disclosed instrument may be operated in one of a plurality of polarity configurations to achieve specific surgical objectives. For example, in a vessel sealing configuration, electrodes 212a and 212b (associated with upper jaw member 210) have a positive polarity (e.g., active electrodes) while electrodes 222a and 222b (associated with lower jaw member 220) have a negative polarity (e.g., return electrodes.) In this generally bipolar configuration, blade 305 is electrically deactivated and severs tissue by physically cutting tissue (e.g., vessel) held between jaws 210, 220. Additionally or alternatively, electrosurgical energy is delivered to a vessel grasped between jaws 210, 220 to effectuate the sealing of the vessel.

In another configuration adapted for cutting, blade 305 is electrically coupled to a source of electrosurgical energy to form an active (e.g., positive) electrode. Electrodes 212a, 212b, 222a, and 222b are configured as a negative, or return, electrode.

During use, blade 305 effectuates cutting via cutting edge 306 and/or the electrosurgical cutting energy delivered between blade 305, cutting edge 306, and electrodes 212a, 212b, 222a, and 222b.

Figure 4:
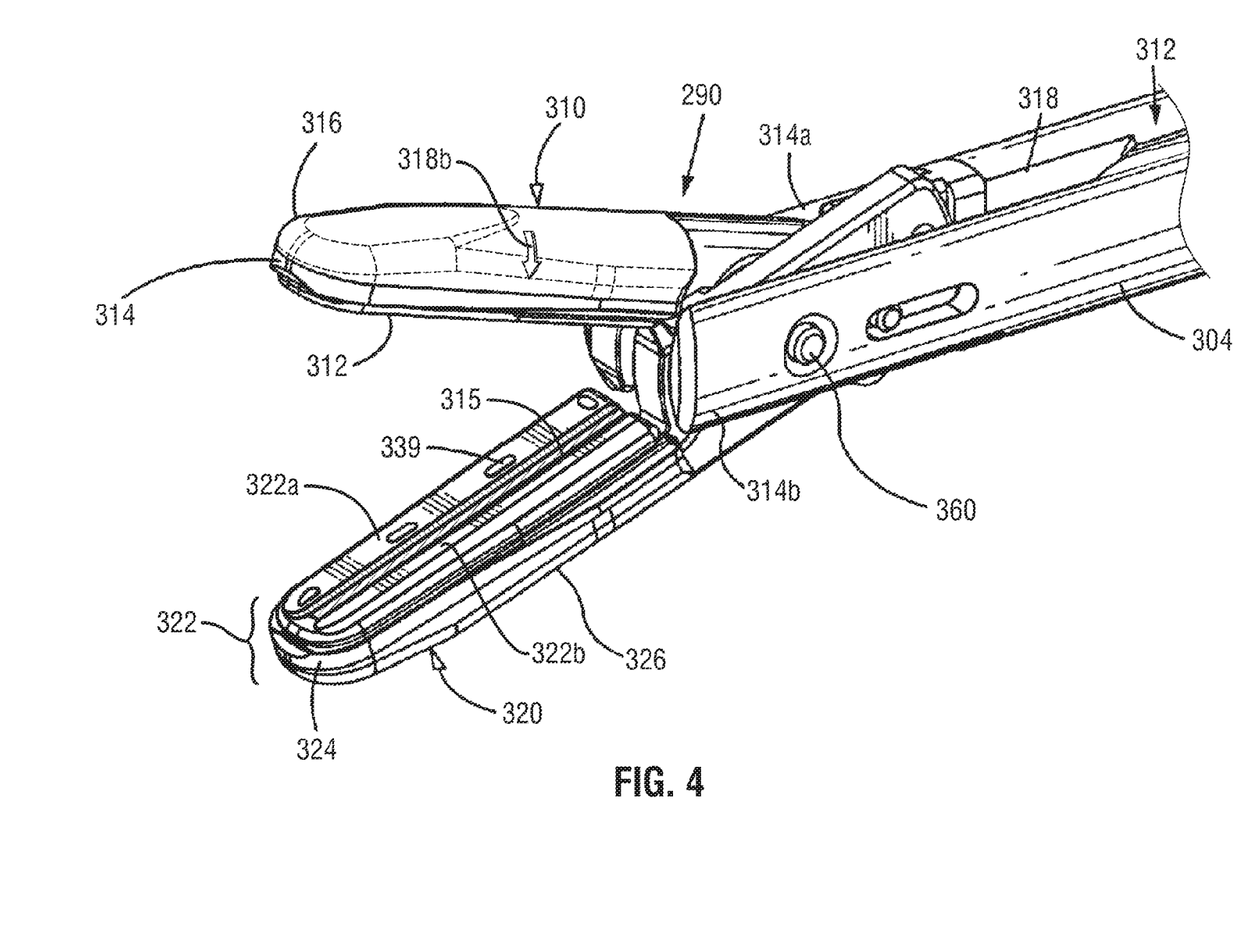
FIG. 4 is an enlarged, left perspective view of another embodiment of a jaw assembly having an asymmetrical electrode in accordance with the present disclosure.
Figure 5:
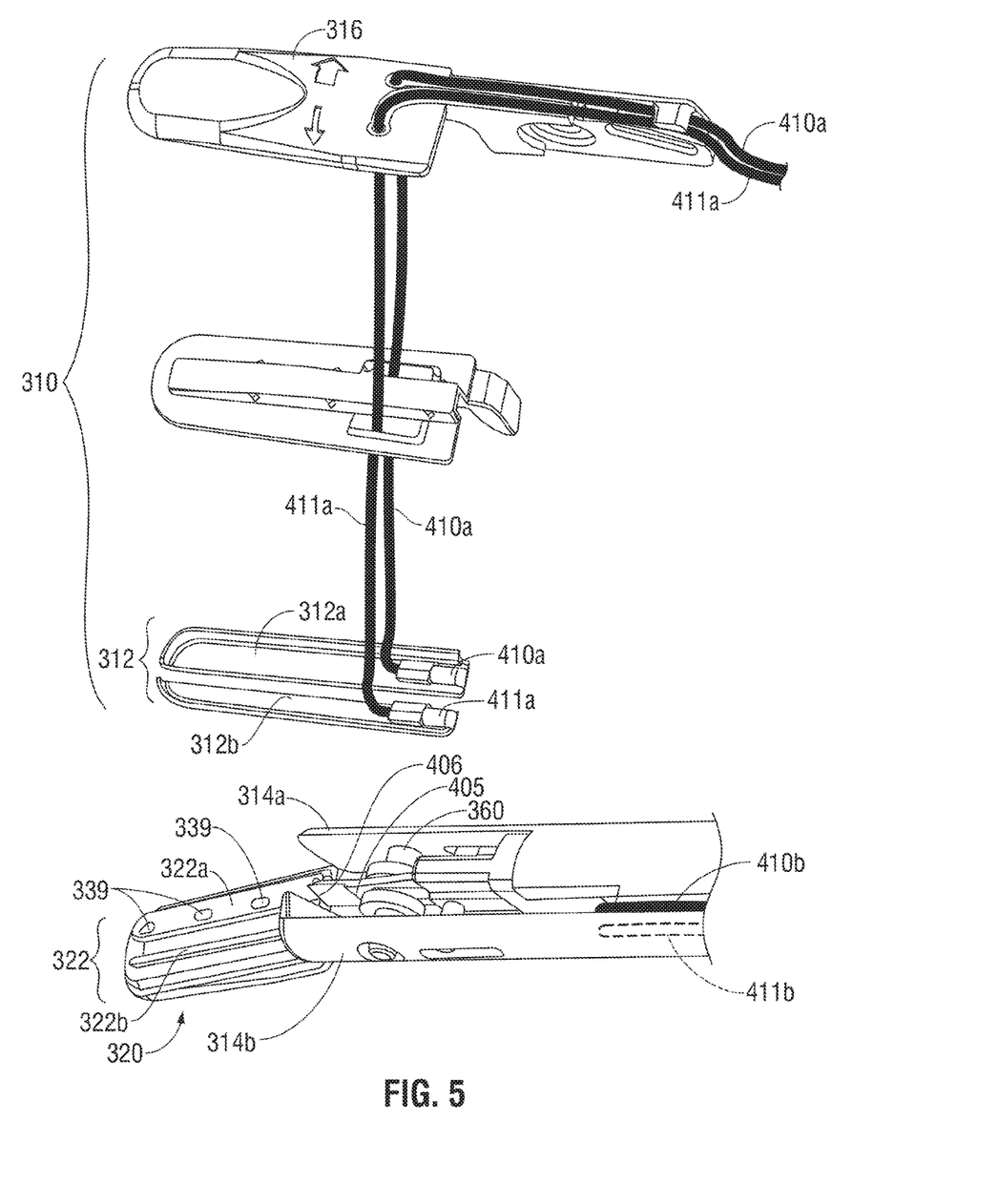
FIG. 5 is an enlarged, partially-exploded view of the FIG. 4 embodiment of a jaw assembly having an asymmetrical electrode in accordance with the present disclosure.

In yet another embodiment depicted in FIGS. 4 and 5, a jaw assembly 290 includes an upper jaw member 310 and a lower jaw member 320. Upper jaw member includes an electrode array 312 having two independent electrodes 312a and 312b. Electrode 312a has a greater surface area than the narrower electrode 312b. Correspondingly, lower jaw member 320 includes a electrode array 322 having two independent electrodes 322a and 322b, wherein electrode 322a has a greater surface area than the narrower electrode 322b. As can be appreciated, electrode arrays 312 and 322 are arranged in a mutually corresponding configuration wherein electrode 312a mates with electrode 322a, and electrode 312b mates with electrode 322b, when the jaw members 310 and 320 are in a closed configuration.

Each of the four electrodes 312a, 312b, 322a, and 322b are independently coupled to one or more sources of electrosurgical energy. As seen in FIG. 5, electrode 312a is coupled to a source of electrosurgical energy by a conductor 410a, and electrode 312b is coupled to a source of electrosurgical energy by a conductor 411a. Electrodes 322a and 322b are coupled to a source of electrosurgical energy by conductors 410b and 411b, respectively. In an envisioned embodiment, electrodes 312a, 312b, 322a, and 322b and knife 405 may be independently selectively assigned to a positive or negative polarity (e.g., designated as an active or return electrode.) In this embodiment a total of 32 electrode configurations are available to the surgeon.

For example, and without limitation, wide electrodes 312a and 322a may be configured in a bipolar arrangement to facilitate vessel sealing on the patient side. On the resection (narrow electrode) side, blade 405 may be configured as an active (+) electrode while narrow electrodes 312b and 322b are configured as a return (−) electrode.

In another embodiment, electrodes may be alternatively or sequentially energized, either individually or in combination, to achieve effectively simultaneous cutting, coagulating, sealing, etc. In another non-limiting example, a source of electrosurgical energy may be configured to provide, during a first time period, vessel sealing energy to a first pair of electrodes 312a and 322a; during a second time period, the source of electrosurgical energy provides coagulation energy to a second pair of electrodes 312b and 322b; and during a third time period, the source of electrosurgical energy provides cutting energy, e.g., sending positive cutting energy to knife 405 and receiving negative cutting energy at electrodes 312a, 322a, 312b, and 322b. The time periods may be of any duration, however it is envisioned that a time period may have a duration of about 0.001 second to about 0.1 second, and continue in round robin fashion during activation (e.g., while activated by the surgeon.) Various electrode combinations, energy profiles, and sequences thereof may be specified, modified, and/or stored for later recall and use by a surgeon.

Figure 7:
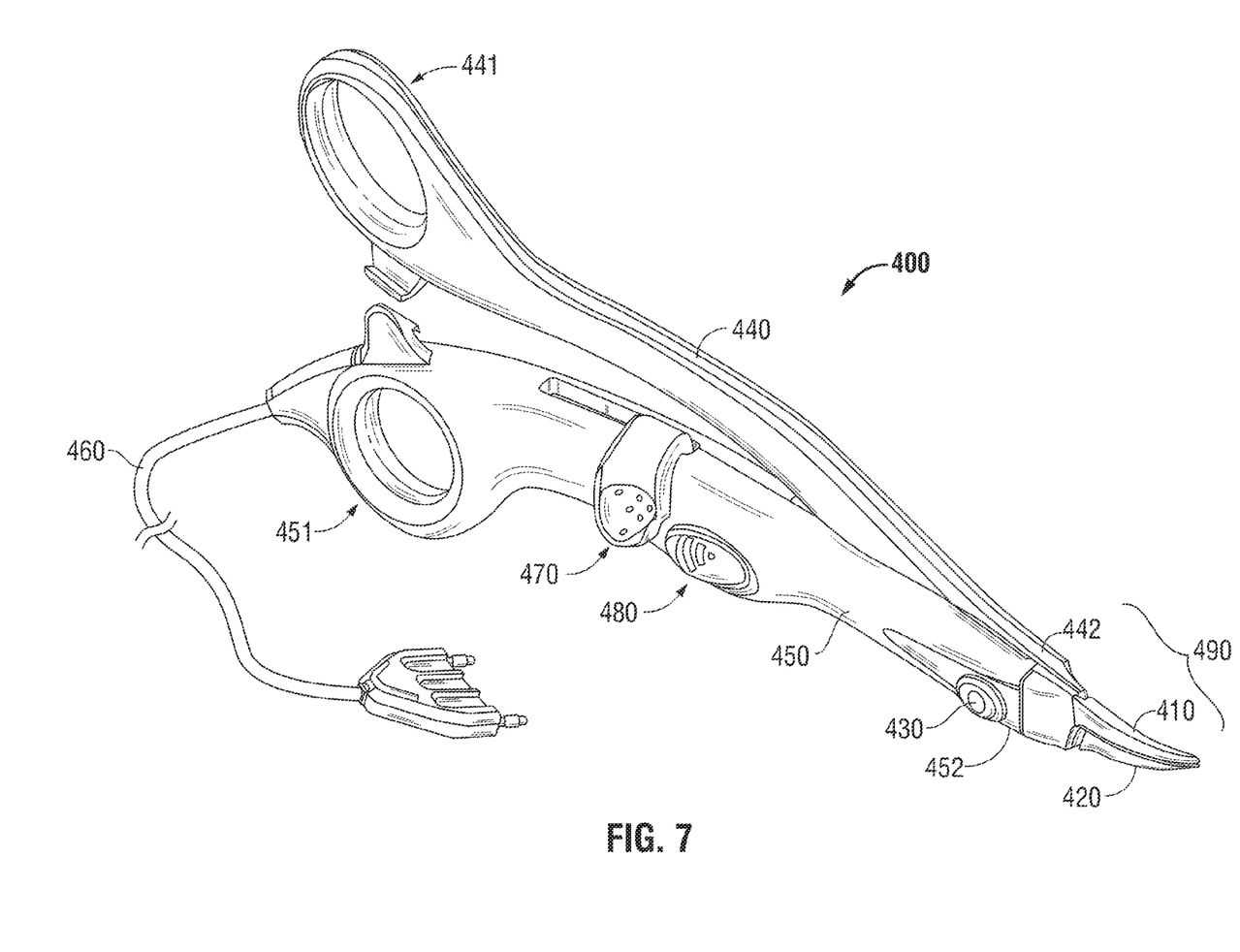
FIG. 7 is a perspective view of another embodiment of a bipolar electrosurgical instrument in accordance with the present disclosure having a jaw assembly that includes an asymmetrical electrode.

FIG. 7 illustrates another embodiment of an electrosurgical instrument 400 in accordance with the present disclosure. Instrument 400 has a generally scissors-like or hemostat-like structure suitable for use in open surgical procedures. Instrument 400 includes elongated shaft portions 440 and 450 each having a proximal end 441 and 451, respectively, and a distal end 442 and 452, respectively. The instrument 400 includes an end effector assembly 490 which is operably coupled to distal ends 442 and 452 of shafts 440 and 450, respectively. The end effector assembly 490 includes pair of opposing jaw members 410 and 420 which are pivotably connected about a pivot pin 430. The two opposing jaw members 410 and 420 of the end effector assembly 490 are pivotable about pin 430 from the open position to the closed position for grasping tissue therebetween. Jaw members 410 and 420 include asymmetrical electrodes (not explicitly shown) arranged as described hereinabove that may be coupled to a source of electrosurgical energy by cable assembly 460. In some embodiments, a source of electrosurgical energy and/or a power source may be included in instrument 400 for "wireless" use. Instrument 400 may include at least one handswitch 480, which may be a slide switch or a pushbutton switch, that is adapted to activate the delivery of electrosurgical energy to tissue. Instrument 400 may additionally or alternatively include a knife actuator 470 that is adapted to actuate a knife (not shown) for dividing tissue grasped between jaws 410 and 420.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector for use with an electrosurgical instrument, comprising:
   a first jaw member and a second jaw member, each jaw member including a first lateral side, a second lateral side, an outer housing and an inner tissue engaging surface, at least one jaw member movable relative to the other jaw member from a first position wherein the jaw members are disposed in spaced relation relative to one another to a second position wherein the jaw members cooperate for grasping tissue therebetween;
   a knife channel defined within and extending centrally along a width of at least the inner tissue engaging surface of the first jaw member; and
   an electrode disposed on at least the inner tissue engaging surface of the first jaw member, the electrode including a first contact area and a second contact area, the first contact area disposed between the knife channel and the first lateral side of the first jaw member, and the second contact area disposed between the knife channel and the second lateral side of the first jaw member;
   wherein a width of the first contact area extending from a first lateral edge of the electrode to a second lateral edge of the electrode is greater than a width of the second contact area extending from a third lateral edge of the electrode to a fourth lateral edge of the electrode, and wherein the width of the first contact area and the width of the second contact area remain substantially uniform along a length of the knife channel.

2. The end effector according to claim 1, wherein the width of the first contact area and the width of the second contact area remain substantially uniform along an entirety of the length of the knife channel.

3. The end effector according to claim 1, wherein a ratio of the width of the first contact area to the width of the second contact area is about 3:1.

4. The end effector according to claim 1, wherein a ratio of the width of the first contact area to the width of the second contact area is in a range of about 1.2:1 to about 10:1.

5. The end effector according to claim 1, wherein the electrode is configured to electrically couple with a source of electrosurgical energy.

6. The end effector according to claim 1, further comprising a visual indicator disposed on the outer housing of at least one jaw member, wherein the visual indicator indicates a position of at least one of the first contact area or the second contact area.

7. The end effector according to claim 1, further comprising a knife having a distal cutting edge and configured to move between a first position where the cutting edge is positioned proximally of the knife channel and a second position where the cutting edge is positioned at least partially within the knife channel.

8. The end effector according to claim 7, wherein the knife is configured to electrically couple with a source of electrosurgical energy.

9. The end effector according to claim 1, wherein the first jaw member defines a longitudinal axis, and wherein the first contact area is axially aligned with the second contact area.

10. An end effector for use with an electrosurgical instrument, comprising:

a first jaw member and a second jaw member, each jaw member including a first lateral side, a second lateral side, an outer housing and an inner tissue engaging surface, at least one jaw member movable relative to the other jaw member from a first position wherein the jaw members are disposed in spaced relation relative to one another to a second position wherein the jaw members cooperate for grasping tissue therebetween, the first jaw member including a knife channel defined therein and extending centrally along a width of the inner tissue engaging surface thereof; and an electrode disposed on at least the inner tissue engaging surface of the first jaw member, the electrode including a first contact area and a second contact area, the first contact area disposed between the knife channel and the first lateral side of the first jaw member, and the second contact area disposed between the knife channel and the second lateral side of the first jaw member;

wherein a width of the first contact area extending from a first lateral edge of the electrode to a second lateral edge of the electrode is greater than a width of the second contact area extending from a third lateral edge of the electrode to a fourth lateral edge of the electrode, and wherein a width of the first jaw member on a first lateral side of the knife channel is substantially equal to a width of the first jaw member on a second lateral side of the knife channel along a length of the knife channel.

11. The end effector according to claim 10, wherein the width of the first contact area and the width of the second contact area remain substantially uniform along an entirety of the length of the knife channel.

12. The end effector according to claim 10, wherein a ratio of the width of the first contact area to the width of the second contact area is about 3:1.

13. The end effector according to claim 10, wherein a ratio of the width of the first contact area to the width of the second contact area is in a range of about 1.2:1 to about 10:1.

14. The end effector according to claim 10, wherein the electrode is configured to electrically couple with a source of electrosurgical energy.

15. The end effector according to claim 10, further comprising a visual indicator disposed on the outer housing of at least one jaw member, wherein the visual indicator indicates a position of at least one of the first contact area or the second contact area.

16. The end effector according to claim 10, further comprising a knife having a distal cutting edge and configured to move between a first position where the cutting edge is positioned proximally of the knife channel and a second position where the cutting edge is positioned at least partially within the knife channel.

17. The end effector according to claim 16, wherein the knife is configured to electrically couple with a source of electrosurgical energy.

18. The end effector according to claim 10, wherein the first contact area is axially aligned with the second contact area.

* * * * *